(12) United States Patent
Tanner et al.

(10) Patent No.: US 9,447,456 B2
(45) Date of Patent: Sep. 20, 2016

(54) SYSTEMS AND METHODS FOR BEAD-FREE DETECTION OF NUCLEOTIDES

(75) Inventors: Carol Tanner, Niles, MI (US); Steven Ruggiero, Niles, MI (US)

(73) Assignee: University of Notre Dame du Lac, Notre Dame, IN (US)

( * ) Notice: Subject to any disclaimer, the term of this patent is extended or adjusted under 35 U.S.C. 154(b) by 10 days.

(21) Appl. No.: 14/114,174

(22) PCT Filed: Sep. 12, 2012

(86) PCT No.: PCT/US2012/054818
§ 371 (c)(1),
(2), (4) Date: Jan. 14, 2014

(87) PCT Pub. No.: WO2013/040008
PCT Pub. Date: Mar. 21, 2013

(65) Prior Publication Data
US 2014/0120539 A1    May 1, 2014

Related U.S. Application Data

(63) Continuation-in-part of application No. PCT/US2012/034899, filed on Apr. 25, 2012.

(60) Provisional application No. 61/533,474, filed on Sep. 12, 2011, provisional application No. 61/688,454, filed on May 14, 2012, provisional application No. 61/517,769, filed on Apr. 25, 2011.

(51) Int. Cl.
*C12Q 1/68* (2006.01)
*G01N 33/48* (2006.01)
*C07H 21/00* (2006.01)

(52) U.S. Cl.
CPC .................................. *C12Q 1/6816* (2013.01)

(58) Field of Classification Search
CPC ......... C12Q 1/68; G01N 33/48; C07H 21/00
See application file for complete search history.

(56) References Cited

U.S. PATENT DOCUMENTS

2009/0325812 A1* 12/2009 Mirkin et al. .................... 506/8

OTHER PUBLICATIONS

Li et al., High-precision sizing of nanoparticles by laser transmission spectroscopy. Applied Optics 49(34) : 6602 (Dec. 2010).*
Vollmer et al., Multiplexed DNA Quantification by Spectroscopic Shift of Two Microsphere Cavities. Biophysical J. 85 :1974 (2003).*
International Preliminary Report on Patentability and Written Opinion of the International Searching Authority of PCT/US2012/54818, date of issuance Mar. 12, 2014, 9 pgs.

* cited by examiner

*Primary Examiner* — Ethan C Whisenant
(74) *Attorney, Agent, or Firm* — Greenberg Traurig, LLP

(57) ABSTRACT

Methods and systems of quantifying a target material in solution include detection of a size change of a hybridized nucleic acid complex, without the use of nanobeads. In particular, the examples include providing a plurality of nucleic acid fragments and a species-specific oligonucleotide tags, measuring the size of the nucleic acid fragments and/or oligonucleotides to predetermine a standard distribution of the solution(s), introducing the oligonucleotides in a solution containing nucleic acid target materials and/or non-target materials, and hybridizing the oligonucleotides with the species-specific target material if present in the solution. The size of the nucleic acid complexes in solution are then measured after hybridization, and the presence or non-presence of the species-specific target material is detected and/or quantified by comparing the measured size of the nucleic acid complexes after hybridization to the standard distribution.

16 Claims, 10 Drawing Sheets

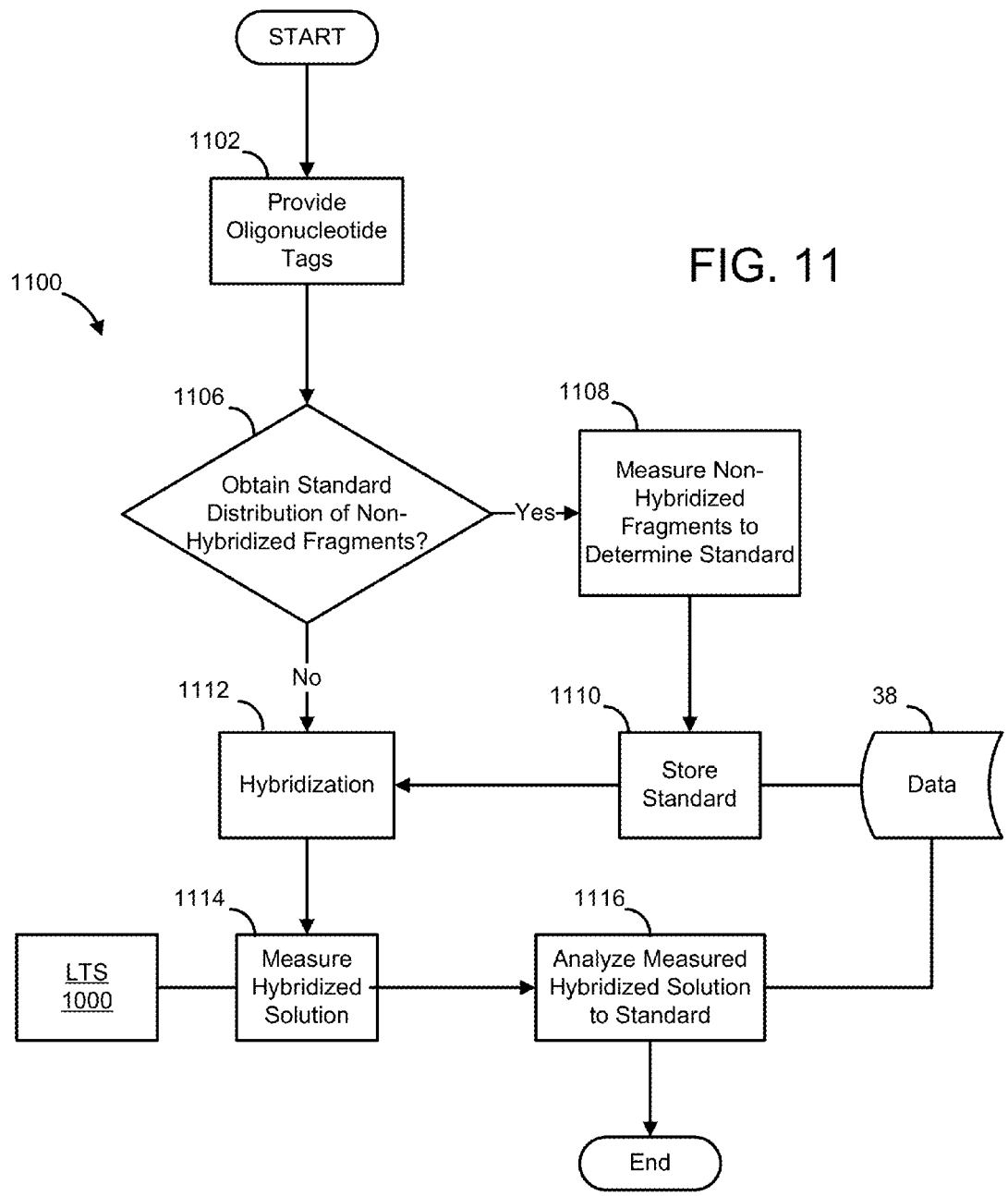

SEQUENCE LISTING

<160> NUMBER OF SEQ ID NOS: 7

<210> SEQ ID NO 1
<211> LENGTH: 28
<212> TYPE: DNA
<213> ORGANISM: Daphnia bugensis

<400> SEQUENCE: 1

-continued

```
acaagttggg ggtggtttag gcgggagt                                              28

<210> SEQ ID NO 2
<211> LENGTH: 28
<212> TYPE: DNA
<213> ORGANISM: Daphnia bugensis

<400> SEQUENCE: 2
tgttcaaccc ccaccaaatc cgccctca                                              28

<210> SEQ ID NO 3
<211> LENGTH: 28
<212> TYPE: DNA
<213> ORGANISM: Daphnia polymorpha

<400> SEQUENCE: 3
ggttcaacca ccccgaatc ctccttcc                                               28

<210> SEQ ID NO 4
<211> LENGTH: 28
<212> TYPE: DNA
<213> ORGANISM: Daphnia magna

<400> SEQUENCE: 4
agttcaacca gtcccagcac cactttcc                                              28

<210> SEQ ID NO 5
<211> LENGTH: 25
<212> TYPE: DNA
<213> ORGANISM: Daphnia bugensis

<400> SEQUENCE: 5
ccttattatt ctgttcggcg tttag                                                 25

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
taaacttcag ggtgaccaaa aaatca                                                26

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
ggtcaacaaa tcataaagat attg                                                  24
```

SYSTEMS AND METHODS FOR BEAD-FREE DETECTION OF NUCLEOTIDES

CROSS REFERENCE TO RELATED APPLICATION

This application is a non-provisional national stage application of International Application No. PCT/US12/54818 entitled "Systems and Methods for Bead-Free Detection of Nucleotides," filed Sep. 9, 2012, which in turn claims priority from U.S. Provisional Application Ser. No. 61/533,474, entitled "Methods and Apparatus for Bead-Free DNA Detection," filed on Sep. 12, 2011, and Provisional Application Ser. No. 61/688,454, filed on May 14, 2012, titled "Method and Apparatus for DNA Detection," both of which are incorporated herein by reference in their entirety. Additionally, International Application No. PCT/US12/54818 is a continuation-in-part of International Application No. PCT/US12/34,899 entitled "Systems and Methods for Detecting and Quantifying a Sequence of Nucleotides," filed Apr. 25, 2012, which in turn claims priority to U.S. Provisional Application Ser. No. 61/517,769, filed on Apr. 25, 2011, the contents of each of which are incorporated herein by reference in their entirety.

FIELD OF THE DISCLOSURE

The present description relates generally to nucleotide detection and more particularly to bead-free systems and methods for detecting and quantifying a sequence of nucleotides.

BACKGROUND OF RELATED ART

Successful detection of a sequence of nucleotides, such as for example deoxyribonucleic acid ("DNA") or ribonucleic acid ("RNA"), can impact many important endeavors such as invasive-species research, medical diagnostics, drug development, environmental health, and the search for exotic life forms. The ability to rapidly and quantitatively distinguish between target and non-target organisms at the point of contact is a challenge for many DNA detection protocols. For example, by some estimates, invasive species cost the US hundreds of billions of dollars annually in agriculture losses, environmental harm, and disease outbreaks. Invasions could potentially be prevented and/or managed more efficiently if detected early. DNA detection also represents a tool in understanding and indicating the presence of genetic diseases such as cancer. Established techniques for genetic profiling involve polymerase chain reaction (PCR), microarrays (lab on a chip techniques, and fluorometric detection). However, such techniques generally have limitations due to high cost, low throughput, and/or high dependence upon sample preparation. Accordingly, there is much to be gained from improvements in DNA detection technology.

Related to DNA detection is the question of whether PCR amplification as a required first step can be eliminated. Work in this area has included systems based on carbon nanotubes, microfluidic streams, silicon nanowire sensors, nanoparticle multilayers, magnetic nanobeads, organic transistors, motion-based sensors using catalytic nanowires, functionalized hydrogels or nanoparticles, DNA sandwich assays, and nanowire arrays. Whereas the portability, functionality, and reliability of these approaches in field settings remain to be seen, based on present findings, laser transmission spectroscopy or light transmission spectroscopy (both of which are intended when referenced as "LTS" in this application) could represent a promising new approach for PCR elimination.

Accordingly there is a documented need for detecting and measuring the presence and quantity of species-specific target nucleotides (e.g., DNA) in solution of which the present disclosure is well suited.

BRIEF DESCRIPTION OF THE DRAWINGS

For a better understanding of the present disclosure, reference may be had to various examples shown in the attached drawings.

FIG. 11 is an example process in flow-chart form that may be carried out using tangible machine readable instructions to implement the example method detecting and quantifying a sequence of nucleotides.

DETAILED DESCRIPTION

The following description of example methods and apparatus is not intended to limit the scope of the description to the precise form or forms detailed herein. Instead the following description is intended to be illustrative so that others may follow its teachings.

The present disclosure describes various example systems and methods useful in the detection and/or quantification of target material, such as for example, DNA material without the use of a foreign detection substance, such as for example, polystyrene nanobeads (e.g. bead-free detection). In the examples disclosed herein, nucleotide fragments, or oligonucleotides are provided so that the nucleotide fragments, oligonucleotides attract and complement target nucleotides. (The terms nucleic acid fragments, nucleotide fragments and oligonucleotides, and oligonucleotides tags are used interchangeably herein.) In one example, the fragments are placed in a solution, and exposed to species-specific target DNA. Once the target nucleotide material hybridizes onto a complementary fragment it creates larger-diameter complexes causing an increase in measurable dimension. Using an instrument capable of detecting the number of particles present at different and discrete sizes, the number of hybridized particles present in a given volume solution can be determined. Analysis of these results can provide qualitative and/or quantitative information regarding the target nucleotide.

In one example, the present systems and methods provide for bead-free DNA detection that is fast, highly selective, quantitative, and/or well suited for many real-world applications including invasive species detection. For instance, the present disclosure in one embodiment discloses a new and useful species-specific DNA detection method and system based on LTS. For instance, in the example method, oligonucleotide tags that are complementary to the target DNA sequence of interest are created. Next, the oligonucleotide tags are exposed to a DNA solution, which may contain the target DNA. In solution, DNA strands containing targets bind to the complementary oligonucleotide tag thereby creating a complex of increased size, which can be measured using LTS.

The example systems and methodology are based on the principle of "smart" particles comprising a specific sequence of nucleic acids, or oligonucleotide tags, that attract specific DNA targets. The examples described herein are meant to replace and/or complement micro-array detection (MAD) and polymerase chain reaction (PCR) amplification and sequencing techniques. In at least one application, the systems and methods described herein only require the testing of a small sample, such as for instance a fraction of a cubic centimeter (cc), that take a relatively short time, such as a minute to process, as well as the pre-preparation of the "smart" particles.

Figure 1:
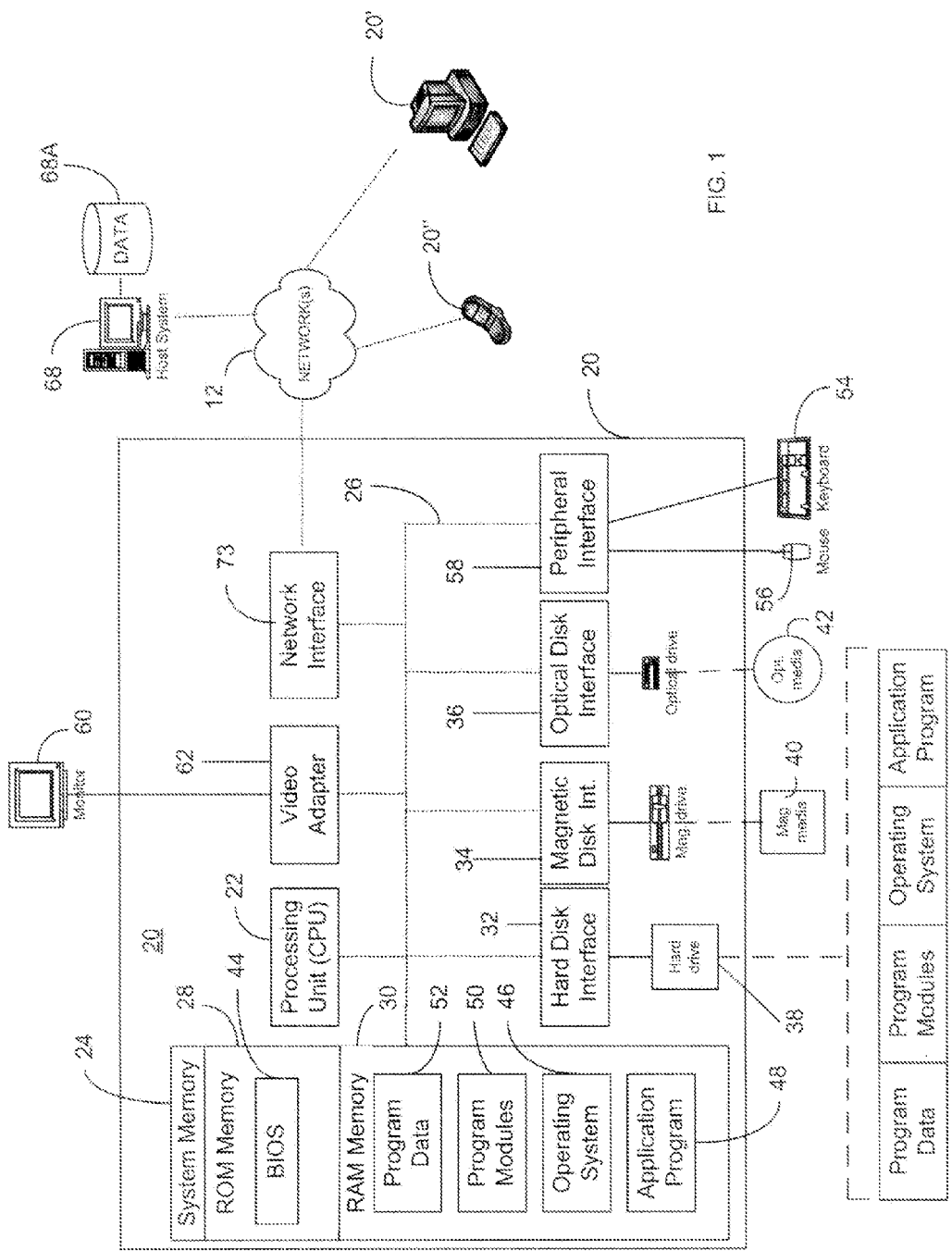
FIG. 1 illustrates in block diagram form components of an example computer network environment suitable for implementing example systems and methods for detecting and quantifying a sequence of nucleotides disclosed herein.

With reference to the figures, the following discloses various example systems and methods for detecting and quantifying a target material. To this end, a processing device 20", illustrated in the exemplary form of a mobile communication device, a processing device 20', illustrated in the exemplary form of a computer system, and a processing device 20 illustrated in schematic form, are provided with executable instructions to, for example, provide a means for receiving and processing information regarding the detection, measuring, and quantification of species-specific DNA in solution. In one example, the illustrated devices 20, 20', 20" are provided with standard network connectivity to a host system server 68 for shared networking, processing, and/or data storage capabilities as desired. Generally, the computer executable instructions reside in program modules which may include routines, programs, objects, components, data structures, etc. that perform particular tasks or implement particular abstract data types. Accordingly, those of ordinary skill in the art will appreciate that the processing devices 20, 20', 20" illustrated in FIG. 1 may be embodied in any device having the ability to execute instructions such as, by way of example, a personal computer, a mainframe computer, a personal-digital assistant ("PDA"), a cellular telephone, a mobile device, a tablet, an ereader, or the like. Furthermore, while described and illustrated in the context of a single processing device 20, 20', 20" those of ordinary skill in the art will also appreciate that the various tasks described hereinafter may be practiced in a distributed environment having multiple processing devices linked via a local or wide-area network whereby the executable instructions may be associated with and/or executed by one or more of multiple processing devices.

For performing the various tasks in accordance with the executable instructions, the example processing device 20 includes a processing unit 22 and a system memory 24 which may be linked via a bus 26. Without limitation, the bus 26 may be a memory bus, a peripheral bus, and/or a local bus using any of a variety of bus architectures. As needed for any particular purpose, the system memory 24 may include read only memory (ROM) 28 and/or random access memory (RAM) 30. Additional memory devices may also be made accessible to the processing device 20 by means of, for example, a hard disk drive interface 32, a magnetic disk drive interface 34, and/or an optical disk drive interface 36. As will be understood, these devices, which would be linked to the system bus 26, respectively allow for reading from and writing to a hard disk 38, reading from or writing to a removable magnetic disk 40, and for reading from or writing to a removable optical disk 42, such as a CD/DVD ROM or other optical media. The drive interfaces and their associated computer-readable media allow for the nonvolatile storage of computer-readable instructions, data structures, program modules, and other data for the processing device 20. Those of ordinary skill in the art will further appreciate that other types of non-transitory computer-readable media that can store data and/or instructions may be used for this same purpose. Examples of such media devices include, but are not limited to, magnetic cassettes, flash memory cards, digital videodisks, Bernoulli cartridges, random access memories, nano-drives, memory sticks, and other read/write and/or read-only memories.

A number of program modules may be stored in one or more of the memory/media devices. For example, a basic input/output system (BIOS) 44, containing the basic routines that help to transfer information between elements within the processing device 20, such as during start-up, may be stored in ROM 28. Similarly, the RAM 30, hard drive 38, and/or peripheral memory devices may be used to store computer executable instructions comprising an operating system 46, one or more applications programs 48 (such as a Web browser), other program modules 50, and/or program data 52. Still further, computer-executable instructions may be downloaded to one or more of the computing devices as needed, for example via a network connection.

To allow a user to enter commands and information into the processing device 20, input devices such as a keyboard 54 and/or a pointing device 56 are provided. While not illustrated, other input devices may include a microphone, a joystick, a game pad, a scanner, a camera, touchpad, touch screen, virtual keyboard, etc. These and other input devices would typically be connected to the processing unit 22 by means of an interface 58 which, in turn, would be coupled to the bus 26. Input devices may be connected to the processor 22 using interfaces such as, for example, a parallel port, game port, firewire, or a universal serial bus (USB). To view information from the processing device 20, a monitor 60 or other type of display device may also be connected to the bus 26 via an interface, such as a video adapter 62. In addition to the monitor 60, the processing device 20 may also include other peripheral output devices, not shown, such as, for example, speakers, cameras, printers, or other suitable device.

As noted, the processing device 20 may also utilize logical connections to one or more remote processing devices, such as the host system server 68 having associated data repository 68A. In this regard, while the host system server 68 has been illustrated in the exemplary form of a computer, it will be appreciated that the host system server 68 may, like processing device 20, be any type of device having processing capabilities. Again, it will be appreciated that the host system server 68 need not be implemented as a single device but may be implemented in a manner such that the tasks performed by the host system server 68 are distributed amongst a plurality of processing devices/databases located at different geographical locations and linked through a communication network. Additionally, the host system server 68 may have logical connections to other third party systems via a network 12, such as, for example, the Internet, LAN, MAN, WAN, cellular network, cloud network, enterprise network, virtual private network, wired and/or wireless network, or other suitable network, and via such connections, will be associated with data repositories that are associated with such other third party systems. Such third party systems may include, without limitation, systems of higher learning, data repositories, systems of third party providers, etc.

For performing tasks as needed, the host system server 68 may include many or all of the elements described above relative to the processing device 20. In addition, the host system server 68 would generally include executable instructions for, among other things, measuring and storing data relating to the solution containing pre-hybridized DNA solution; measuring and storing data relating to hybridized DNA solution; and analyzing data collected relating to the pre-hybridized and hybridized DNA solutions; etc.

Communications between the processing device 20 and the host system server 68 may be exchanged via a further processing device, such as a network router (not shown), that is responsible for network routing. Communications with the network router may be performed via a network interface component 73. Thus, within such a networked environment, e.g., the Internet, World Wide Web, LAN, cloud, or other like type of wired or wireless network, it will be appreciated that program modules depicted relative to the processing device 20, or portions thereof, may be stored in the non-transitory memory storage device(s) of the host system server 68.

Figure 2:
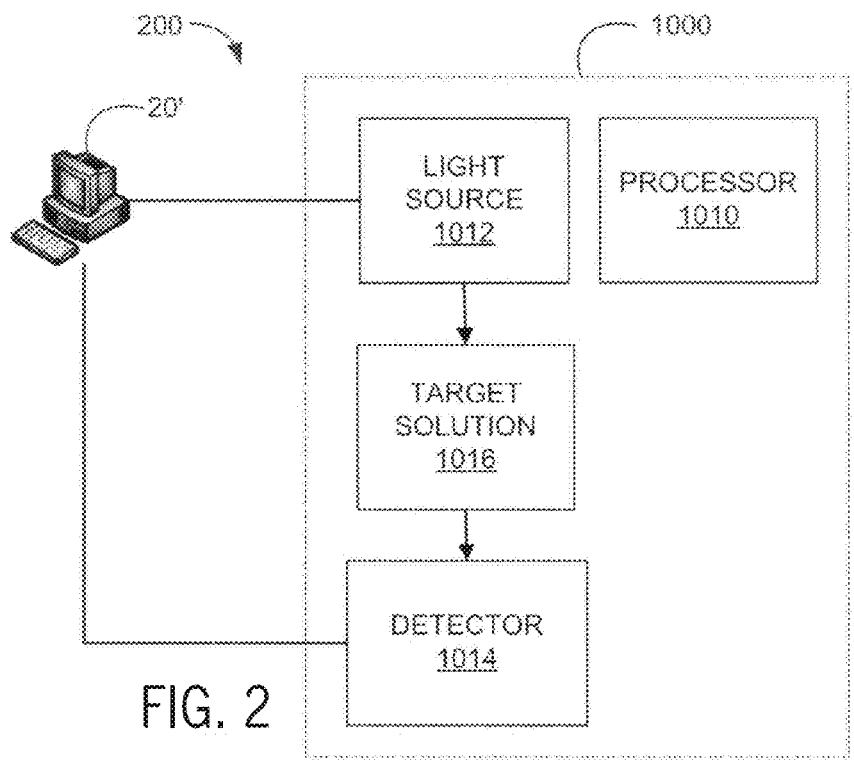
FIG. 2 illustrates in block diagram form an example system for detecting and quantifying a sequence of nucleotides.

Referring to FIG. 2, there is illustrated an overview of an example system 200 for providing quantitative and rapid target detection by, for instance, laser transmission spectroscopy in accordance with an example of the present disclosure. In the present example, the system 200 includes at least one the devices 20, 20', 20", and a transmission-based particle measurement system, such as for example a LTS system 1000 as described in co-pending U.S. patent application Ser. No. 13/125,613. More particularly, the example system 200 is a new DNA detection technique using LTS to, in one example, measure the size of functionalized polystyrene nanobeads, and in another example, to measure the size of DNA complexes comprising oligonucleotides, which may or may not be hybridized with target DNA, without the use of polystyrene nanobeads. The LTS transmission-based particle measurement system 1000 is adapted for characterizing nanoparticles capable and as such, for rapidly determining the size, shape, and number density of nanoparticles in suspension, and generally includes a processor 1010, a light source 1012 such as a tunable wavelength laser, a detector 1014, and a target solution 1016.

Figure 3:
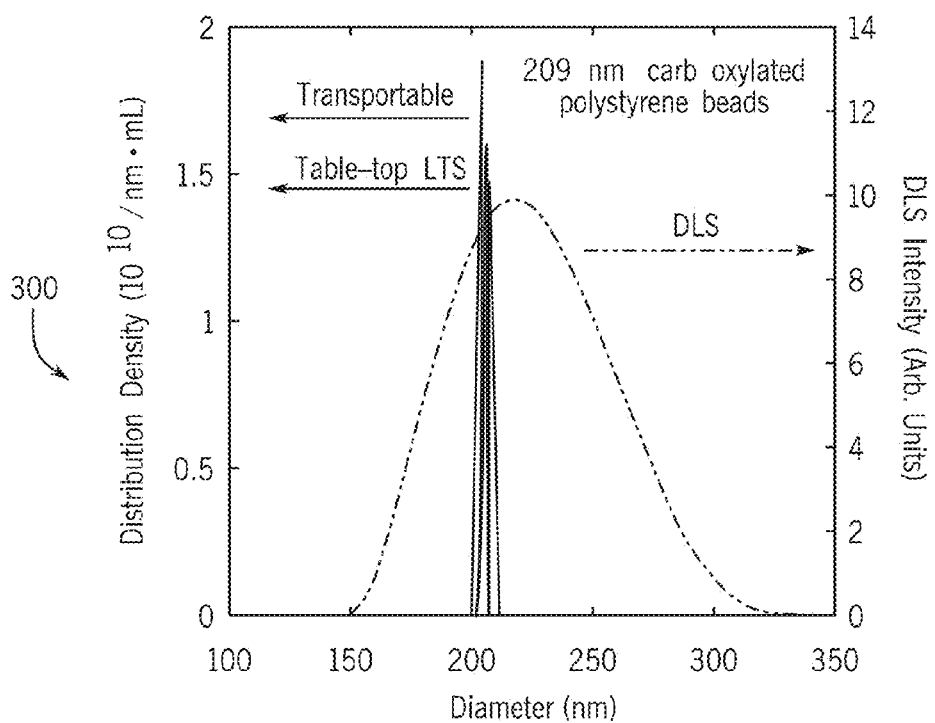
FIG. 3 is an example plot of distribution density versus diameter for transmission-based measurement techniques utilized to detect hybridization in the system of FIG. 2.

In this example, the LTS system 1000 is based on wavelength-dependent light extinction whereas other prior known light based detection techniques rely on diffraction or scattering. For comparison, FIG. 3 illustrates a typical particle size distribution 300 for an example 209 nm carboxylated nanobeads in accordance with one aspect of the present disclosure. More particularly the distribution 300 is a comparison plot of the particle size distributions obtained for carboxylated nanobeads in water using an example table-top sized LTS (plot 302) having a data acquisition time of approximately an hour, an example transportable LTS (plot 304) with a data acquisition time of approximately 100 ms and an analysis time of approximately less than three minutes, and an example commercially available dynamic light scattering (DLS) instrument (plot 306). As is evident from the distribution 300, the LTS plots (302, 304) is shown to have at least five times higher resolution with the capability of quantitatively measuring the number density of nanoparticles as compared with the dynamic light scattering (plot 306), which can only give a much broader relative measure of the particle size distribution. This resolution may be especially advantageous in the size range typically associated with DNA detection such as, for example, approximately 50 to 100 nm. It will be understood by one of ordinary skill in the art, however, that the target detection may be any suitable target, and/or any suitable size range as desired.

Figure 4:
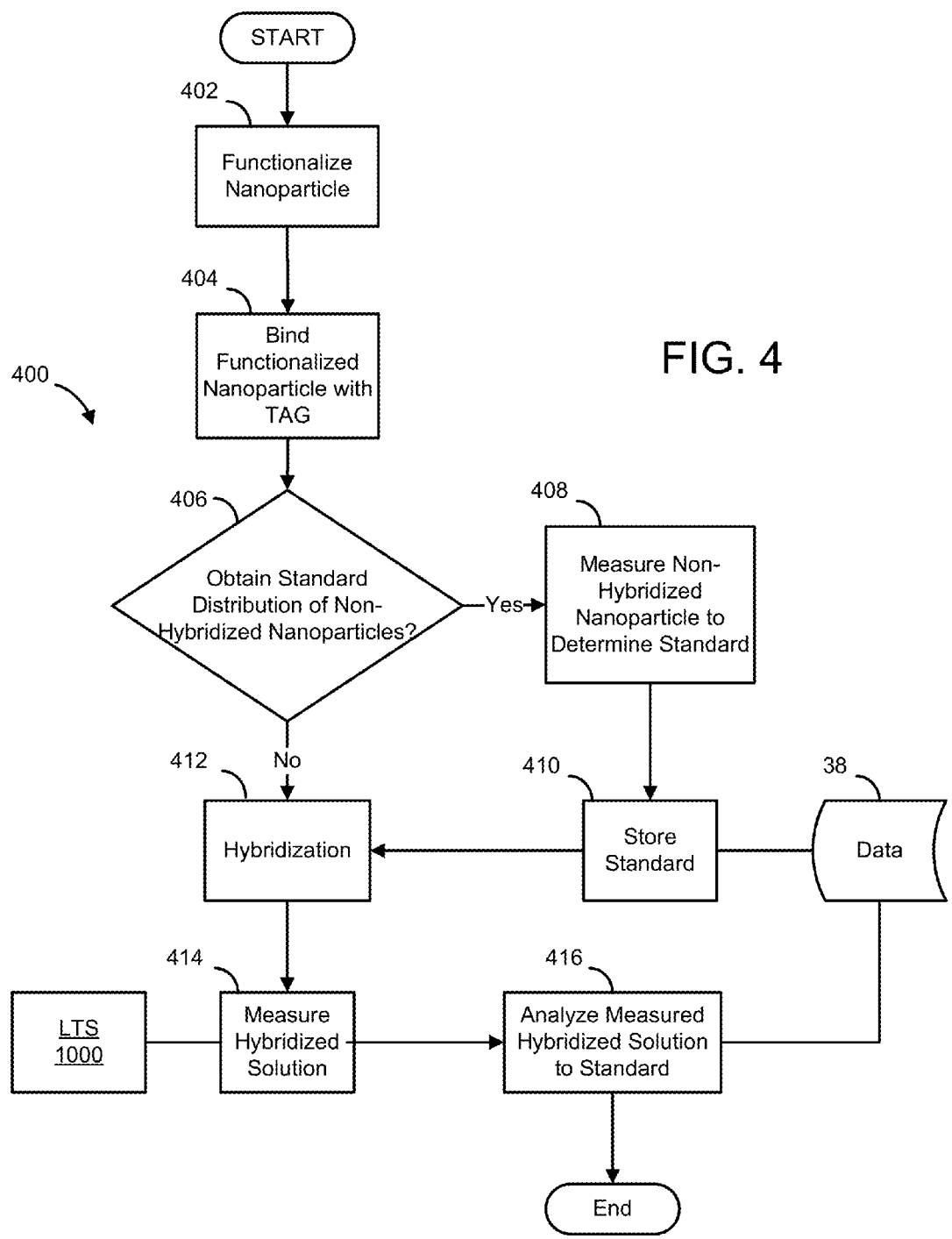
FIG. 4 is an example process in flow-chart form that may be carried out using tangible machine readable instructions to implement the example method detecting and quantifying a sequence of nucleotides.
Figure 5:
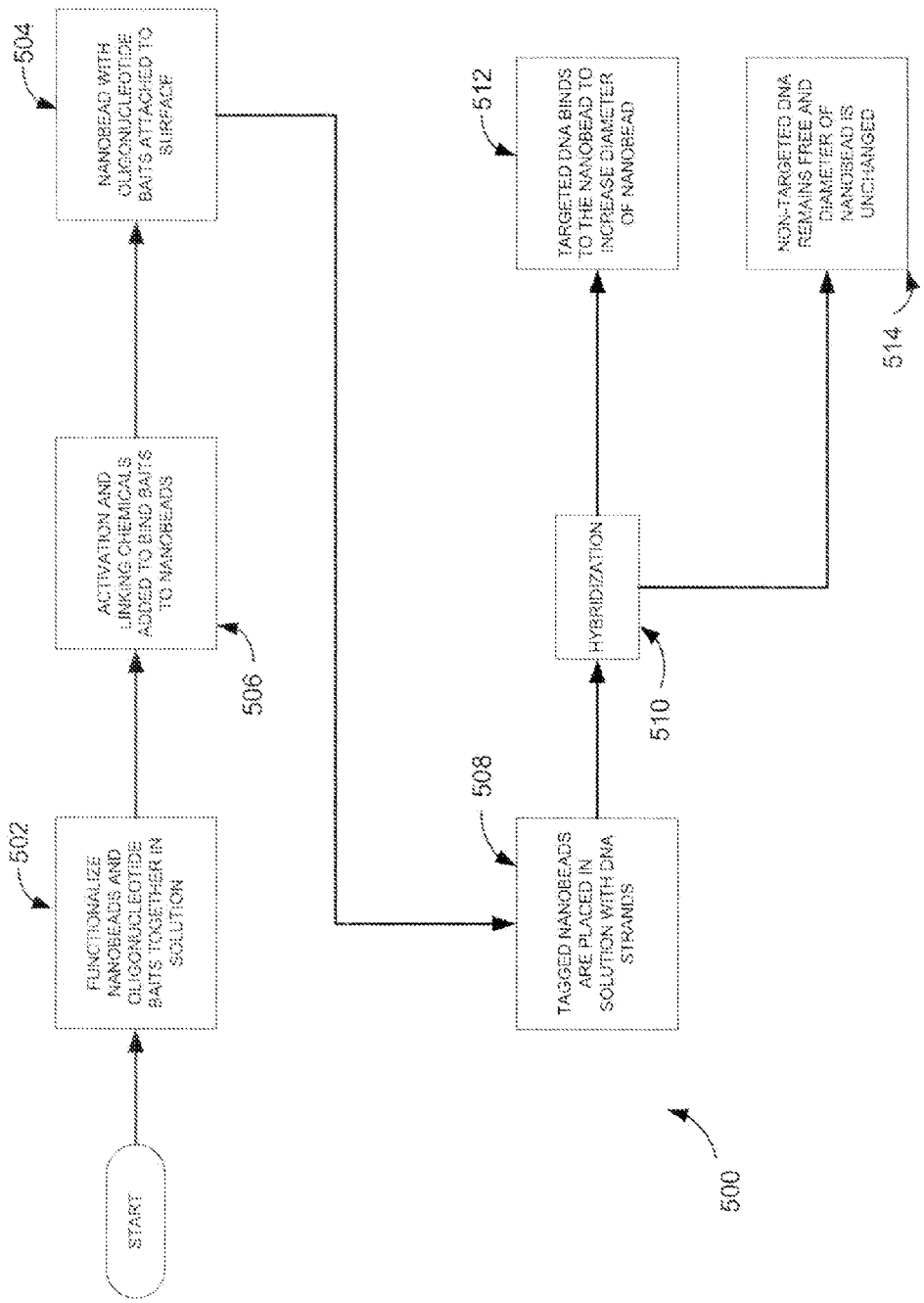
FIG. 5 is an example process in schematic form that may be carried out using tangible machine readable instructions to implement the example method detecting and quantifying a sequence of nucleotides.

Turning now to FIGS. 4 and 5, there is illustrated an overview of an example method that may be utilized by the example system 200 for providing quantitative and rapid target detection as described herein. In the example method, a process 400 generally comprises the preparation of functionalized nanobeads, the binding of the functionalized beads to a target material such as DNA, the measurement of the size of the beads after sufficient time for binding, and the comparison of the measurements to the predetermined standard and/or control solution to confirm and/or quantify the binding of the target mater to the beads as desired.

For example, in one example, the process 400 begins at a block 402, where a plurality of nanospheres are each functionalized, such as for example, a plurality of functionalized polystyrene nanospheres. The functionalized nanospheres are then placed in solution with a tag at a block 404. In one example, the utilized tag comprises oligonucleotide bait introduced in solution with the functionalized nanobeads. It is at this point that data regarding the size of the functionalized nanobeads and associated tags may be measured by the LTS system 1000 to provide a predetermined standard as necessary at block 406. In particular, if standardization and/or predetermined data is required, the LTS system 1000 may be utilized to measure the pre-hybridized nanobead size at a block 408, and the data may be stored in the system memory 24 and/or the data repository 68A. It will be appreciated by one of ordinary skill in the art that the predetermined measurement steps 408, 410 may not be necessary where the device 20 is previously provided with such information in its memory 24 and/or is adapted to readily retrieve such information form a qualified source such as, for instance, the central server 68 and/or data repository 68A.

As illustrated in FIG. 5, one specific example process 500 utilizes a plurality of carboxylated polystyrene nanobeads 502 functionalized with species-specific oligonucleotides, acting as tags that bind to species-specific DNA sequences targets 504. As will be appreciated, the LTS utilized system 1000 has more than sufficient resolution, approximately 3 nm, to detect the large diameter increase (100s of nm) that occurs when the DNA strands containing the targets hybridize with the tags on the surface of the functionalized nanobeads. More specifically, with the described LTS system 1000, the number of beads and their change in diameter are quantifiably measured. In at least one example, the utilized LTS system 1000 can distinguish a species-specific DNA sequence of the invasive quagga mussel (*Dreissena bugensis*) from those of the evolutionarily related sister species, zebra mussel (*Dreissena polymorpha*), and the common planktonic cladoceran, (*Daphnia magna*). In one example, the methods presented use pre-screened PCR amplified mitochondrial DNA fragments from quagga mussel as targets to demonstrate the general efficacy of LTS for DNA detection, but it will be appreciated that any suitable target may be detected. Similarly, in this instance, polystyrene was selected because of the availability of uniformly sized nanobeads of this material, but it will be appreciated that any suitable nanostructure, including other and/or additional nanobeads may be utilized. More specifically, carboxylated polystyrene beads with a manufacturer's stated diameter of 209 nm were chosen because this size is well within the example LTS system's operational range, and the expected diameter change is significant and easily detected.

solution to detect the size of the nanobeads at a block 414. The measured solution may be quantified by distinguishing the measured nanobeads to distinguish hybridized species-specific target detection from non-hybridized nanobeads by comparing the measured size distribution with the standard and/or control at block 416. The identified differences in the comparison, therefore, will provide a rapid quantitative species-specific target detector as disclosed.

Referring again to FIG. 5, again the example tag used for functionalization is a 28 base oligonucleotide that is species-specific to the quagga mussel (*D. bugensis*). The biomarker is within the mitochondrial cytochrome c oxidase subunit I (COI) gene. As illustrated below in Table 1, a comparison among species-specific oligonucleotide tags and biomarkers used to demonstrate the sensitivity of LTS to target and non-target DNA sequences shows the differences between target and non-target sequences. As is seen in Table 1, across the 28 bases of the tag, the quagga mussel (target species) differs by 7 nucleotides from the zebra mussel (*D. polymorpha* non-target species) and by 12 nucleotides from the cladoceran (*Daphnia magna* also a non-target species).

TABLE 1

| Species Description | DNA biomarker 28-base sequences |
|---|---|
| species-specific tag quagga | A C A A G T T G G G G G T G G T T T A G G C G G G A G T (SEQ ID NO.: 1) |
| quagga mussel (*D. bugensis*) | T G T T C A A C C C C C A C C A A A T C C G C C C T C A (SEQ ID NO.: 2) |
| zebra mussel (*D. polymorpha*) | G G T T C A A C C A C C C C C G A A T C C T C C T T C C (SEQ ID NO.: 3) |
| cladoceran (*Daphnia magna*) | A G T T C A A C C A G T C C C A G C A C C A C T T T C C (SEQ ID NO.: 4) |

In this embodiment, the carboxyl groups on the surface of the beads were activated with 2-(N-morpholino) ethanesulfonic acid (MES) buffer at pH 6.0 at 506. A linker carbodiimide, 1-ethyl-3-(3-dimethylaminopropyl), was added to the bead solution to provided amino groups that covalently bond to both the carboxyl group of the beads and the carboxyl terminus of a species-specific tags. Constant agitation with the addition of ethanolamine was used to quench the conjugated beads after functionalization. The prepared beads were stored in a buffer solution at 4° C. to maintain separation and suspension prior to their use.

Returning now to FIG. 4, once the nanobeads are prepared, the nanobeads are combined in a solution with the target material at a block 412. As is well known in the art, the functionalized nanobeads will hybridize with the correct target material, and will not hybridize with non-specific target material. Once sufficient time for hybridization has passed, the LTS system 1000 may be utilized to measure the Genomic DNA used for PCR amplification was extracted from quagga and zebra mussel muscle tissue and from the whole cladoceran organism using, for example, a Qiagen DNEasy extraction kit available from Qiagen, Inc. Amplification of the partial COI gene was then performed on each extraction. In brief, PCR reactions consisted of 1 ml of genomic DNA, 0.75 U Taq polymerase and 10×PCR buffer, available from 5 Prime, Inc., 2.5 mM Mg(OAc)2, 10 nmol of each dNTP, primers (final concentration 0.2 mM), and deionized water for a total reaction volume of 25 mL. The PCR thermal program consisted of an initial denaturation step for 1 minute at 94° C. followed by 30 cycles of 30 seconds at 94° C., 45 seconds at 48° C., and 1 minute at 72° C., then a final elongation for 8 minutes at 72° C. Table 2 illustrates the molecular biomarkers utilized for the example PCR amplification. In this example, LCO-1490 and HCO-2198 are universal invertebrate primers as is known by one of ordinary skill in the art.

TABLE 2

| Species | Forward Primer | Reverse Primer |
|---|---|---|
| quagga mussel (*D. bugensis*) | (quagga COI-F) 5'-CCTTATTATTCTGTTCGGCGTTTAG-3' (SEQ ID NO.: 5) | (HCO-2198) 5'-TAAACTTCAGGGTGACCAAAAAATCA-3' (SEQ ID NO.: 6) |

TABLE 2-continued

| Species | Forward Primer | Reverse Primer |
|---|---|---|
| zebra mussel (D. polymorpha) | (LCO-1490) 5'-GGTCAACAAATCATAAAGATATTG-3' (SEQ ID NO.: 7) | (HCO-2198) 5'-TAAACTTCAGGGTGACCAAAAAATCA-3' (SEQ ID NO.: 6) |
| cladoceran (Daphnia magna) | (LCO-1490) 5'-GGTCAACAAATCATAAAGATATTG-3' (SEQ ID NO.: 7) | (HCO-2198) 5'-TAAACTTCAGGGTGACCAAAAAATCA-3' (SEQ ID NO.: 6) |

After the PCR reactions were completed, the PCR amplified DNA from each organism was denatured by heating to 95° C. for 2 minutes, then immediately chilled on ice for 2 minutes, then 10 µL of each were combined with 20 µL of functionalized beads (concentration $1.04 \times 10^9$/mL) at 48° C. for one minute (see FIG. 5, steps 508, 510, 512, and 514). The three DNA-plus-bead samples were placed in quartz spectrometer cells and analyzed by LTS with respect to a reference cell containing all the components used in preparing the DNA-plus-bead samples, excluding the DNA and the tagged beads. A control sample, which contained the tagged beads without DNA, was also run with respect to the same reference sample.

Figure 6A:
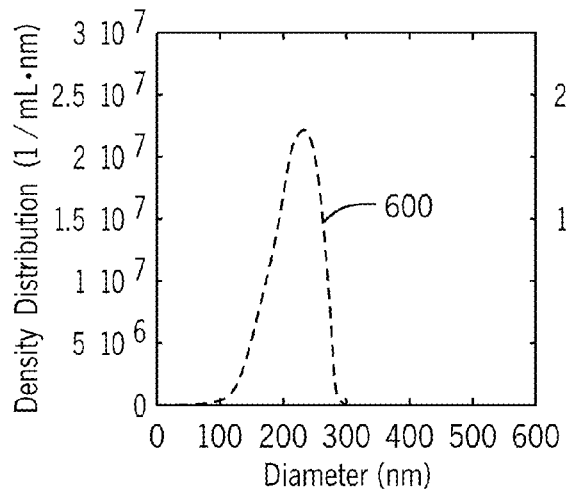
FIGS. 6A-6D are example plots of distribution density versus diameter for the transmission-based measurement techniques utilized to detect hybridization and non-hybridization in the system of FIG. 2.
Figure 6B:
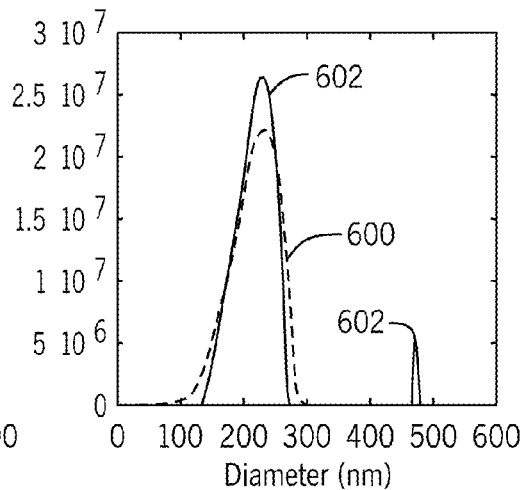
Figure 6C:
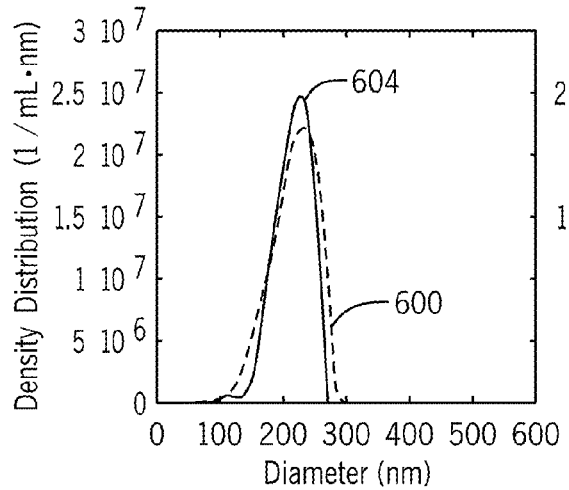
Figure 6D:
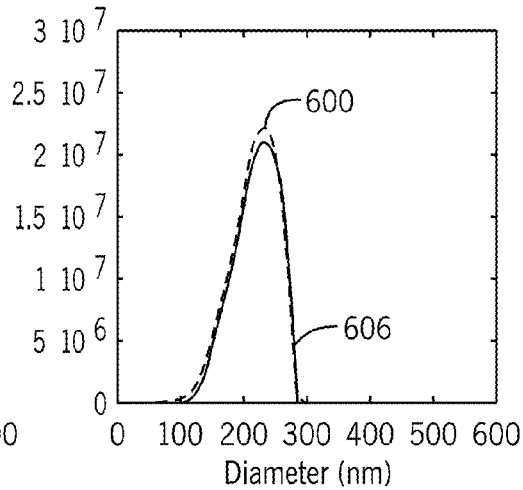

Referring to FIGS. 6A-D, the particle size distribution 600 as measured by the LTS system 1000 of beads functionalized with quagga mussel tags is shown in FIG. 6A. FIG. 6B illustrates an overlay of the particle size distribution 600 over the measured size distribution 602 of quagga functionalized beads exposed to denatured quagga mussel DNA, e.g., the target material. In the example distribution 602, positive target DNA detection is indicated by the peak at 468 nm. FIG. 6C illustrates a size distribution 604 of quagga functionalized beads exposed to denatured zebra mussel DNA, which in this example is a non-target material. Finally, FIG. 6D illustrates a size distribution 606 of quagga functionalized beads exposed to denatured cladoceran DNA, which again is another non-target material. Accordingly, FIGS. 6C and D clearly show an absence of particles at larger sizes indicate a negative response with no target DNA detected.

Particularly, FIG. 6A shows the LTS system 1000 results for the control sample where tagged beads unexposed to DNA are seen to have a maximum in the particle-size distribution at 230 nm. As noted previously, this data may be used as the predetermined standard stored in the device 20 and utilized in the comparison block 416. Next, FIGS. 6C and 6D show the results for tagged beads exposed to the DNA of non-target species, where the LTS system 1000 analysis gives a similar particle size distribution with only a single peak at 230 nm, indicating a negative DNA detection result. In sharp contrast, FIG. 6B shows that after exposure to target DNA some tagged beads increased in size after hybridization, producing a new peak in the particle-size distribution at 468 nm, indicating positive DNA detection of the target species. As indicated by the ratio of the areas under each peak, approximately 2 percent of the beads hybridized with the target DNA. This was likely due to an excess of functionalized beads, whereby not all functionalized beads were hybridized. The results imply that the amplified PCR product, here the mitochondrial COI fragment from quagga mussel, should remain flexible in solution which would account for the observed size increase of 238 nm.

This example shows that the laser transmission spectroscopy system 1000 can be used as a generalized method for rapid, quantitative species-specific DNA detection, and furthermore can distinguish genetic variations within a given species (e.g., different genetic populations of organisms, strains, etc.). Specifically, the LTS system 1000 in conjunction with functionalized nanobeads successfully discriminated species-specific target DNA from closely related non-target DNA. Two closely related species, both invasive to North American freshwater systems (*Dressina bugensis* and *D. polymorpha*) and a common planktonic cladoceran (*Daphnia magna*) were used to demonstrate the speed, sensitivity, and selectivity of the LTS system 1000 as a DNA detection method.

Figure 7A:
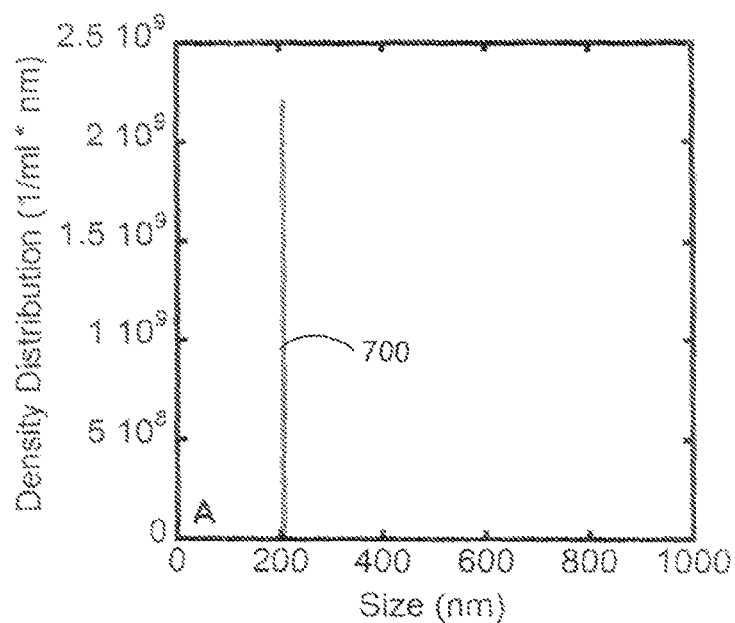
FIGS. 7A and 7B are example plots of distribution density versus diameter for another transmission-based measurement technique utilized to detect hybridization in the system of FIG. 2.

In yet another example of the steps that may be employed by the process 400, 200 nm polystyrene nanospheres functionalized with an amine group on the surface were measured with the LTS system 1000. FIG. 7A shows the measured results 700 in the form of a size versus density distribution. The particles are measured to be 206 nm. In the illustrated example, the 6 nm deviation from 200 nm is likely caused by the functionalization of the amine group to the 200 nm polystyrene nanospheres.

Figure 7B:
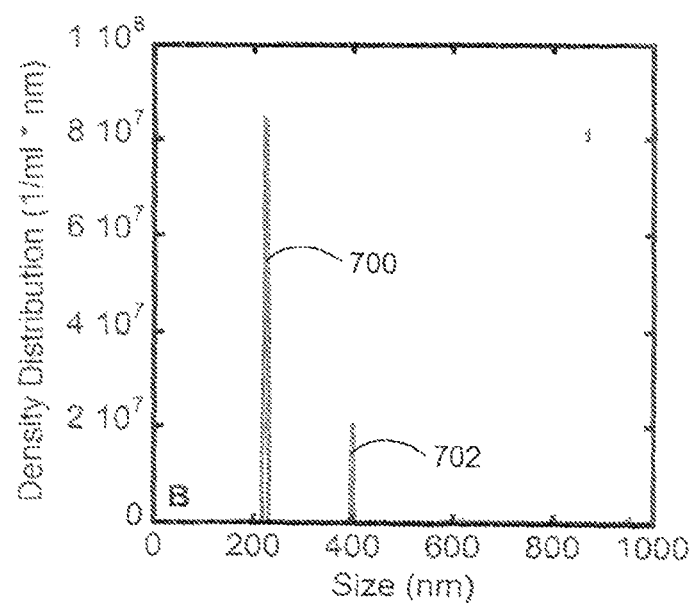

PCR primers were attached to the 200 nm functionalized polystyrene nanospheres through a series of chemical processes and constant shaking of the PCR primer/nanospheres mixture. A storage buffer was added at the end to ensure no more chemical processes occurred. FIG. 7B shows the measured results utilizing the LTS system 1000 for the 200 nm particles with the PCR primers attached. As shown an increased size of the spheres is measured at 222 nm. The example PCR primers utilized are approximately 15 base pairs and the size of each base pair is approximately 1 nm. Thus the sphere can have a maximum increase of approximately 30 nm in diameter. However, taking into account that the primers are not rigid, bending and folding of the primers is likely to occur in a liquid medium and thus the actual increase in size is typically smaller than 30 nm and an increase of approximately 16 nm is therefore reasonable.

As can be seen in FIG. 7B, larger particles 702 are measured, namely at approximately 400 nm, 610 nm, and 960 nm. These are aggregations due to the chemical binding process of the PCR primers to the functionalized nanospheres. As previously described, the example polystyrene nanospheres may then be exposed to a target DNA for further processing.

Figure 8:
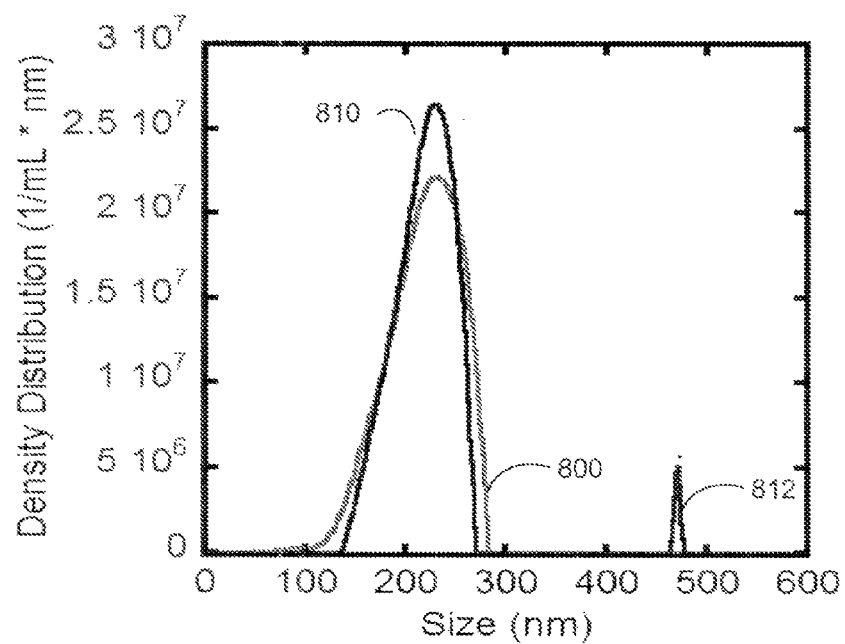
FIGS. 8 and 9 are example plots of distribution density versus diameter for yet another transmission-based measurement technique utilized to detect hybridization in the system of FIG. 2.
Figure 9:
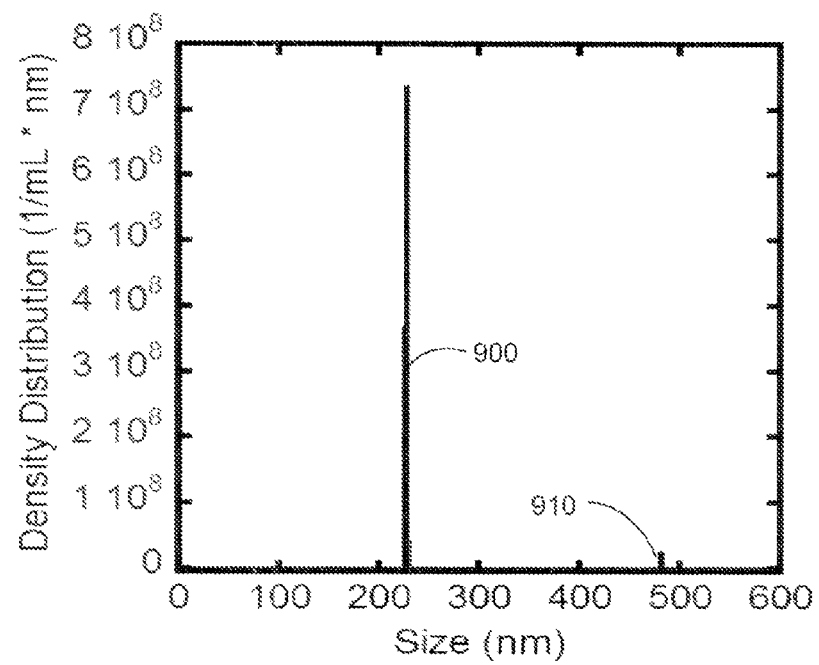

In yet another example, illustrated in FIGS. 8 and 9, a density distribution of non-hybridized functionalized particles 800 versus functionalized particles 810 with no target DNA attached is shown. Additionally, this graph shows the results of a density distribution of functionalized particles with target DNA attached at 812. FIG. 9, meanwhile, shows the results from another sample analysis comparing the density distribution of the non-hybridized particles 900 versus functionalized particles 910 with target DNA attached. In particular, the distribution 900 illustrates the poly beads with the TAGs attached only, while the distribution 910 illustrates the polybeads when the target DNA is attached to the TAGs. Both the distributions have a peak at approximately 230 nm, illustrating the beads with only TAGs and no DNA attached. For the distribution 910, there is an additional peak at 468 nm, illustrating the beads with the DNA attached to them. Accordingly, the amount of DNA added was sufficient to bind to some of the beads, but not enough to fully bind to all the beads, hence the presence of a two peaks.

Referring again to FIG. 2, as previously noted, in another example of the system 200 a new DNA detection technique using laser LTS may be used to measure the size of hybridized DNA complexes without the use of any foreign substance, such as for example the polystyrene nanobeads 502. More specifically, in this example, the LTS transmission-based particle measurement system 1000 is adapted for characterizing a target nucleotide in solution without the use of a polystyrene nanobead 502 by utilizing an oligonucleotide tag, that is, a specific sequence of nucleic acids that attracts target DNA or RNA as the case may be.

For instance, as illustrated in FIG. 11, another example process 1100 may be utilized by the example system 200 for providing quantitative and/or rapid target detection as described herein. In this disclosed example, the process 1100 generally comprises the preparation of oligonucleotide tags, the binding of the oligonucleotide tags to a target material such as DNA, the measurement of the size of the DNA complexes after sufficient time for binding, and the comparison of the measurements to the predetermined standard and/or control solution to confirm and/or quantify the binding of the target matter to the oligonucleotide tags as desired.

For instance, in this example, the process 1100 begins at a block 1102, where a solution containing oligonucleotide tags is provided, sourced, synthesized, or created from, for example, DNA fragments, RNA fragments and/or any other suitable fragment as desired.

As disclosed, the example oligonucleotides can be created by denaturing target nucleic acids in a thermal cycler by heating the nucleic acid solution. More specifically, in one example a target, or species-specific, DNA may be placed in a reference solution of deionized water. The target DNA fragments are denatured by heating the DNA solution in a thermal cycler at 95° C. for two minutes in a sample tube. The DNA solution is then immediately chilled on ice for two minutes to prevent the denatured DNA fragments from recombining.

It is at this point that data regarding the size of the oligonucleotide tags alone in solution may be measured by the LTS system 1000 to provide a predetermined standard as necessary at block 406. In particular, if standardization and/or predetermined data is required, the LTS system 1000 may be utilized to measure the pre-hybridized DNA fragments in the reference solution at a block 408, and the data may be stored in the system memory 24 and/or the data repository 68A. In this example, the LTS system 1000 may measure the size of the oligonucleotide tags in the solution of deionized water.

It will be appreciated by one of ordinary skill in the art that the predetermined measurement steps 408, 410 may not be necessary where the device 20 is previously provided with such information in its memory 24 and/or is adapted to readily retrieve such information from a qualified source such as, for instance, the central server 68 and/or data repository 68A.

One example method utilizes a plurality of DNA oligonucleotides of specific nucleotide sequences that attract species-specific DNA sequence targets. As will be appreciated, the LTS utilized system 1000 has more than sufficient resolution, e.g., approximately 2-3 nm, to detect the large diameter increase (in the order of 100 nm) that occurs when the DNA strands containing the targets hybridize with the oligonucleotide tags. More specifically, with the described LTS system 1000, the number of DNA fragments and oligonucleotide tags, and their change in diameter are quantifiably measured. Still further, the LTS system 1000 has sufficient resolution to distinguish between non-hybridized and hybridized targets. Specifically, in at least one instance, the utilized LTS system 1000 can distinguish a species-specific DNA sequence of the invasive quagga mussel (*Dreissena bugensis*) from those of the evolutionarily related sister species, zebra mussel (*Dreissena polymorpha*), and the common planktonic cladoceran, (*Daphnia magna*). Additionally, the example methods presented use pre-screened PCR amplified mitochondrial DNA fragments from quagga mussel as targets to demonstrate the general efficacy of LTS for DNA detection, but it will be appreciated that any suitable target may be detected.

Returning again to FIG. 11, once the solution containing oligonucleotide tags, is combined with the target DNA material at a block 1112. As is well known to one of ordinary skill in the art, the target DNA fragments will hybridize with the correct oligonucleotide tag, and will not hybridize with non-specific target material. Of course, it will be appreciated that methods may be used to encourage hybridization between the solution containing the target DNA fragments and oligonucleotides tags, such as for example heating the combined DNA solution and the TAGs, etc. For instance, the entire solution may be heated to 72° C. for 5 minutes to allow the material to hybridize.

Once sufficient time for hybridization has passed, the LTS system 1000 may be utilized to measure the solution to detect the size of the DNA complexes at a block 1114. DNA target detection may be distinguished by observing hybridized target DNA complexes as opposed to non-hybridized DNA fragments through comparison of the measured size distributions with the standard and/or control at block 1116. The identified differences in the comparison, therefore, will provide a rapid quantitative species-specific target detector as disclosed.

In one example of the process 1102, the DNA tag was a 28 base oligonucleotide that is species-specific to the quagga mussel (*D. bugensis*) similar to the previously described example. The biomarker is within the mitochondrial cytochrome c oxidase subunit I (COI) gene. As illustrated below in Table 3, a comparison among species-specific oligonucleotide tags and biomarkers used to demonstrate the sensitivity of LTS to target and non-target DNA sequences shows the differences between target and non-target sequences. Referring again to Table 1, across the 28 bases of the tag, the quagga mussel (target species) differs by 7 nucleotides from the zebra mussel (*D. polymorpha* non-target species) and by 12 nucleotides from the cladoceran (*Daphnia magna* also a non-target species).

TABLE 3

| Species Description | DNA biomarker 28-base sequences |
|---|---|
| species-specific tag quagga | A C A A G T T G G G G G T G G T T T A G G C G G G A G T (SEQ ID NO.: 1) |
| quagga mussel (D. bugensis) | T G T T C A A C C C C C A C C A A A T C C G C C C T C A (SEQ ID NO.: 2) |
| zebra mussel (D. polymorpha) | G G T T C A A C C A C C C C C G A A T C C T C C T T C C (SEQ ID NO.: 3) |
| cladoceran (Daphnia magna) | A G T T C A A C C A G T C C C A G C A C C A C T T T C C (SEQ ID NO.: 4) |

Genomic DNA used for PCR amplification was extracted from quagga and zebra mussel muscle tissue and from the whole cladoceran organism using, for example, a Qiagen DNEasy extraction kit available from Qiagen, Inc. Amplification of the partial COI gene was then performed on each extraction. In brief, PCR reactions consisted of 1 ml of genomic DNA, 0.75 U Taq polymerase and 10×PCR buffer, available from 5 Prime, Inc., 2.5 mM Mg(OAc)2, 10 nmol of each dNTP, primers (final concentration 0.2 mM), and deionized water for a total reaction volume of 25 mL. The PCR thermal program consisted of an initial denaturation step for 1 minute at 94° C. followed by 30 cycles of 30 seconds at 94° C., 45 seconds at 48° C., and 1 minute at 72° C., then a final elongation for 8 minutes at 72° C. Here again, Table 4 illustrates the molecular biomarkers utilized for the example PCR amplification. In this example, LCO-1490 and HCO-2198 are universal invertebrate primers as is known by one of ordinary skill in the art.

(FIG. 10A), and a combined solution of DNA fragments and TAGs (FIG. 10B) in accordance with the process 1100. In particular FIGS. 10A-B show size versus density distribution as measured by the LTS system 1000.

Figure 10A:
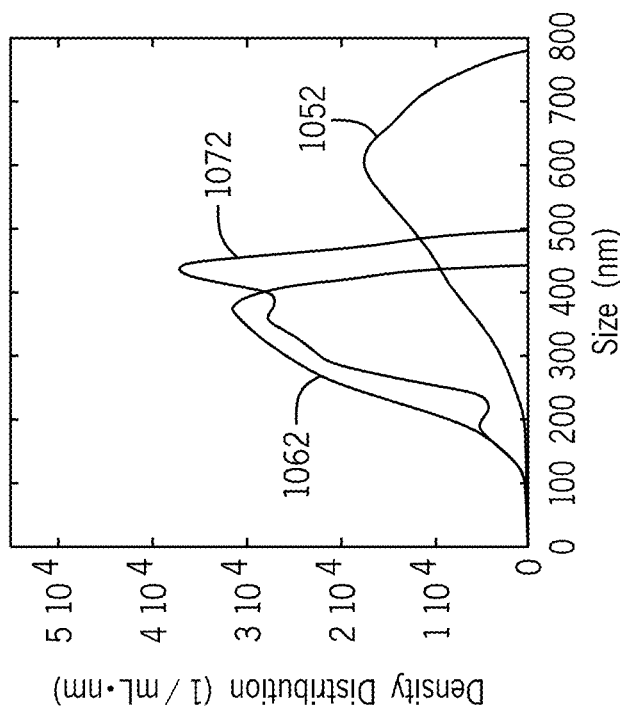
FIGS. 10A-10B are example plots of distribution density versus diameter for the transmission-based measurement techniques utilized to detect hybridization and non-hybridization in the system of FIG. 2.
Figure 10B:
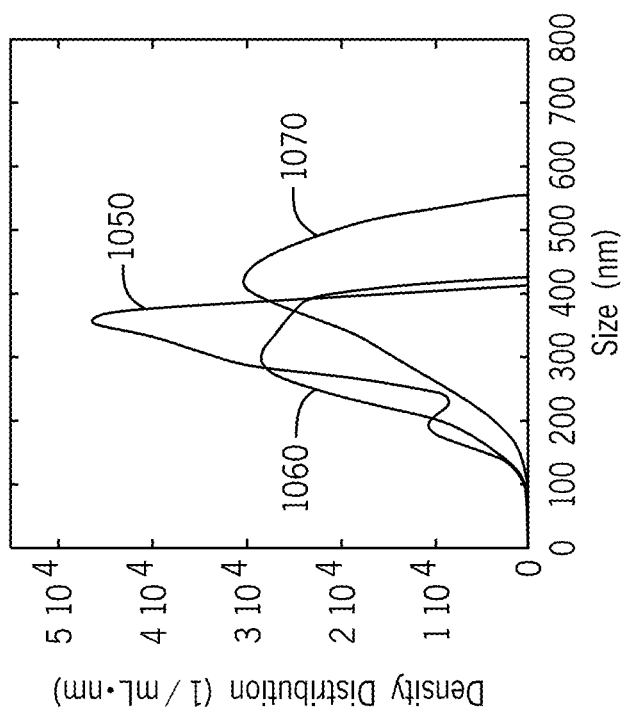

FIG. 10A shows the LTS system 1000 results for the control sample containing the background DNA before it is exposed to the oligonucleotide tags. In this example, the DNA solution contains quagga mussel (D. bugensis) DNA fragments, zebra mussel (D. polymorpha) DNA fragments, and cladoceran (Daphnia magna) DNA fragments. FIG. 10A illustrates the particle size distribution 1050 of quagga mussel (D. bugensis) DNA fragments, which peaks at approximately 350 nm. The particle size distribution 1060 of cladoceran (Daphnia magna) DNA fragments peaks at approximately 300 nm and the particle size distribution 1070 of zebra mussel (D. polymorpha) DNA fragments peaks at approximately 410 nm. As noted previously, this data may

TABLE 4

| Species | Forward Primer | Reverse Primer |
|---|---|---|
| quagga mussel (D. bugensis) | (quagga COI-F) 5'-CCTTATTATTCTGTTCGGCGTTTAG-3' (SEQ ID NO.: 5) | (HCO-2198) 5'-TAAACTTCAGGGTGACCAAAAAATCA-3' (SEQ ID NO.: 6) |
| zebra mussel (D. polymorpha) | (LCO-1490) 5'-GGTCAACAAATCATAAAGATATTG-3' (SEQ ID NO.: 7) | (HCO-2198) 5'-TAAACTTCAGGGTGACCAAAAAATCA-3' (SEQ ID NO.: 6) |
| cladoceran (Daphnia magna) | (LCO-1490) 5'-GGTCAACAAATCATAAAGATATTG-3' (SEQ ID NO.: 7) | (HCO-2198) 5'-TAAACTTCAGGGTGACCAAAAAATCA-3' (SEQ ID NO.: 6) |

After the PCR reactions were completed, the PCR amplified DNA from each organism was denatured by heating to 95° C. for 2 minutes, then immediately chilled on ice for 2 minutes to prevent the denatured DNA fragments from recombining. Then the tag material, for example oligonucleotides, are added to the solution containing the DNA fragments, and the entire solution is heated to 72° C. for 5 minutes to allow the hybridization of the target DNA to the denatured DNA fragments. The combined solution is then stored in a cooled environment, such as, for example a refrigerator.

The combined DNA solution was analyzed by LTS 1000 with respect to the reference solution, which in one example contains the background PCR product which comprises deionized water and all the components used in preparing the DNA fragments excluding the DNA fragments. A control sample, which contained the DNA fragments without the tag material, was also run with respect to the same reference sample.

Referring now to FIGS. 10A-B, those figures show example particle size distributions from a control sample be used as the predetermined standard stored in the device 20 and utilized in the comparison block 1116.

Next, FIG. 10B, shows the LTS system 1000 results for the solution containing both target and non-target DNA fragments after exposure to oligonucleotide tags of quagga mussel (D. bugensis). FIG. 10B shows that the particle size distribution 1052 of quagga mussel (D. bugensis) increases significantly while the particle size distribution 1062 of cladoceran (Daphnia magna) and the particle size distribution 1072 of zebra mussel (D. polymorpha) remain comparatively unchanged. In particular, the particle size distribution 1052 shows an increase in particle size reflecting the hybridization of the quagga mussel (D. bugensis) DNA target fragments with the quagga mussel (D. bugensis) oligonucleotide tag material. Accordingly, FIG. 10B clearly shows the presence of quagga mussel (D. bugensis) particles at larger sizes indicating the presence of the target DNA, quagga mussel (D. bugensis) in the tested solution.

Referring now to FIGS. 12A-D, those figures show example particle size distributions from a negative control sample comprising oligonucleotides tags exposed to non-target background DNA fragments (FIGS. 12A and 12C), and a solution of target and non-target DNA exposed oligonucleotide tags including the target DNA fragments (FIGS. 12B and 12D) in accordance with the process 1100. In particular FIGS. 12A-D show size versus density distribution as measured by the LTS system 1000.

Figure 12A:
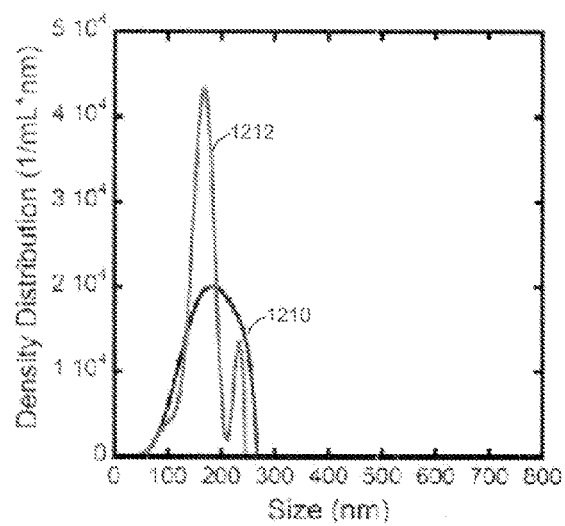
FIGS. 12A-12D are example plots of distribution density versus diameter for the transmission-based measurement techniques utilized to detect hybridization and non-hybridization in the system of FIG. 2.

FIG. 12A shows the LTS system 1000 results for a negative control sample containing PCR amplified non-target DNA fragments in solution, before 1210 and after 1212 it is exposed to oligonucleotide tags. In this example, the pre-hybridization particle size distribution 1210 of the background PCR amplified product peaks at approximately 184 nm. Following exposure of the PCR amplified non-target DNA fragments to the oligonucleotide tags the particle size distribution 1212 of the background PCR amplified product combined with non-target DNA peaks at approximately 170 nm. The change in nanoparticle size is relatively small indicating, as expected, that the oligonucleotides did not hybridize with non-target DNA to form larger DNA complexes.

Figure 12B:
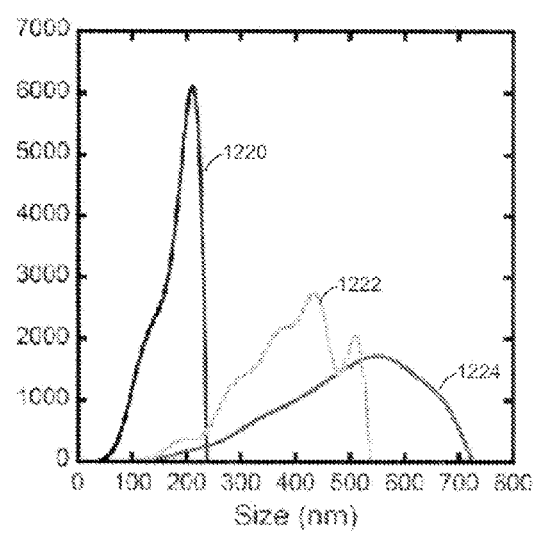

FIG. 12B shows the LTS system 1000 results showing detection of a target DNA in a solution containing oligonucleotide tags. In this example, the pre-hybridization solution particle size distribution 1220 of containing target DNA peaks at approximately 212 nm before it is exposed to the oligonucleotide tags. In a first scenario the solution containing oligonucleotide tags is exposed to target DNA and other background, non-target DNA fragments, forming a particle size distribution 1222 that peaks at approximately 486 nm. In a second scenario the solution containing oligonucleotide tags solution is exposed to only target DNA to form a particle size distribution 1224 that peaks at approximately 552 nm. The hybridized particle size distributions 1222 and 1224 both indicate a large increase in particle size, which reflects the hybridization of oligonucleotides tags and target DNA to form larger DNA complexes.

Figure 12C:
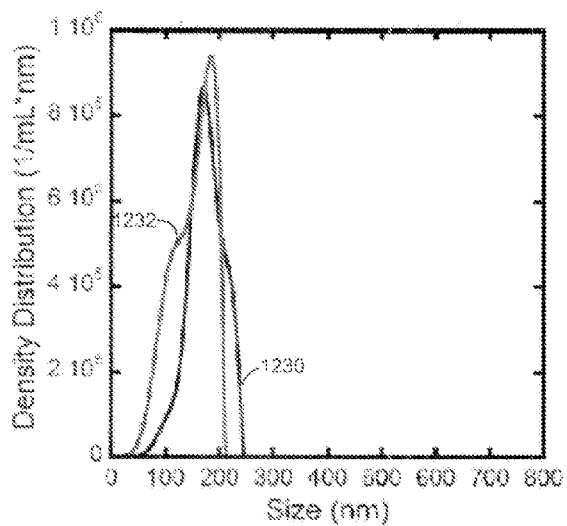

FIG. 12C shows the LTS system 1000 results for a negative control sample containing a non-target DNA solution, before 1230 and after 1232 it is exposed to oligonucleotide tags. In this example, the particle size distribution 1230 of the non-target DNA solution peaks at approximately 172 nm. Following exposure to the oligonucleotide tags, the particle size distribution 1232 of the non-target DNA peaks at approximately 188 nm. After exposure of the non-target DNA fragments to the oligonucleotide tags, the change in nanoparticle size is relatively small indicating, as expected, that the oligonucleotides did not hybridize with target DNA to form larger DNA complexes.

Figure 12D:
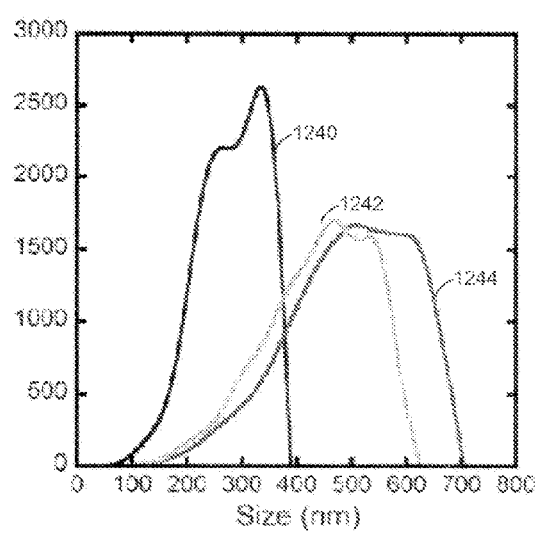

FIG. 12D shows the LTS system 1000 results showing detection of target DNA in solution which also contains non-target DNA after exposure to oligonucleotide tags. In this example, the pre-hybridization solution particle size distribution 1240 containing both target and non-target DNA fragments peaks at approximately 336 nm before the mixed solution is exposed to the oligonucleotide tags. In a first scenario the target and non-target DNA solution is exposed to oligonucleotide tags and the resulting solution particle size distribution 1242 peaks at approximately 470 nm. In a second scenario a solution containing only target DNA is exposed to oligonucleotide tags and the resulting solution particle size distribution 1244 peaks at approximately 510 nm. The particle size distributions 1242 and 1244 for solutions following exposure of the DNA fragments to the oligonucleotide tags both indicate a the presence of larger particles in solution, which reflects the hybridization of oligonucleotide tags and target DNA to form larger DNA complexes.

These examples show that the LTS system 1000 can be used as a generalized method for rapid, quantitative species-specific DNA detection, and furthermore can distinguish genetic variations within a given species (e.g., different genetic populations of organisms, strains, etc.). Specifically, the LTS system 1000 in conjunction with oligonucleotide tags, successfully discriminated species-specific target DNA from closely related non-target DNA. Two closely related species, both invasive to North American freshwater systems, quagga mussel (*D. bugensis*) and zebra mussel (*D. polymorpha*) and a common planktonic cladoceran (*Daphnia magna*) were used to demonstrate the speed, sensitivity, and selectivity of the LTS system 1000 as a DNA detection method.

As previously noted, the LTS system 1000 may be used to identify the particle sizes of materials suspended in a solution. The example LTS system 1000 described herein employs particle size measurements, particle distribution measurements, absolute particle number measurements, and absolute particle density measurements via light transmission rather than scattering-based techniques. As a result, particle sizes may be measured down to 10 nm or less, and up to 3000 nm or more, in which the range is a function of, in part, the light source(s), detector(s), and/or other components employed. The example LTS system 1000 described herein also improves upon particle identification by providing information related to a particle major axis and a minor axis.

While the example transmission-based particle measurement system 1000 has been previously described in the applicants' related application U.S. patent application Ser. No. 13/125,613, and thus not repeated herein, it will be appreciated that other suitable measurement systems may be utilized as desired, including light and/or non-light measurement system as appropriate. Additionally, while the device 20 and the LTS system 1000 have been shown to identify particle sizes and densities of materials suspended in a solution as separate and coupled apparatus, one or more of the elements and/or devices illustrated herein may be combined, divided, re-arranged, omitted, eliminated and/or implemented in any other way.

Although certain example methods, apparatus, and articles of manufacture have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A method of quantifying a target material in solution comprising:

providing a plurality of nucleic acid fragments in a solution;

exposing the solution comprising the plurality of nucleic acid fragments to a plurality of oligonucleotide tags such that at least one of the nucleic acid fragments may hybridize with at least one of the oligonucleotide tags;

measuring the size of particles in the solution, including measuring at least one of the size of the plurality of nucleic acid fragments or the hybridized nucleic acid fragments and oligonucleotide tags, after a sufficient time for hybridization;

determining a size distribution of the measured size of particles in the solution; and at least one of detecting or quantifying nucleic acid material by comparing the determined size distribution of the measured size of the particles in solution to a standard distribution of non-hybridized nucleic acid fragments to determine whether at least a subset of the nucleic acid fragments have hybridized with the oligonucleotide tags wherein no bead(s) is/are used in the quantification of said target material.

2. A method as defined in claim 1, wherein the oligonucleotide tags are a sequence of nucleotides.

3. A method as defined in claim 1, wherein measuring the size of particles in the solution comprises utilizing a light measurement system.

4. A method as defined in claim 3, wherein the light measurement system is a laser transmission spectroscopy or light transmission spectroscopy (LTS) system.

5. A method as defined in claim 1, wherein the oligonucleotide tags are at least one of a deoxyribonucleic acid (DNA) or a ribonucleic acid (RNA).

6. A method as defined in claim 1, wherein the plurality of nucleic acid fragments in solution are subject to polymerase chain reaction (PCR) to amplify the at least one of the nucleic acid fragments across several orders of magnitude.

7. A method as defined in claim 1, wherein at least one of the plurality of nucleic acid fragments comprises a target DNA fragment which is species-specific.

8. A method as defined in claim 1, wherein the standard distribution of non-hybridized nucleic acid fragments is determined by measuring the size of particles in the solution prior to hybridization.

9. A method as defined in claim 8, wherein measuring the size of the particles in the solution prior to hybridization comprises utilizing a light measurement system.

10. A method as defined in claim 8, wherein measuring the size of the particles in the solution occurs prior to exposing the solution comprising the plurality of nucleic acid fragments to the plurality of oligonucleotide tags.

11. A method as defined in claim 1, wherein the standard distribution of non-hybridized nucleic acid fragments is a pre-determined standard.

12. A method as defined in claim 1, wherein providing the plurality of nucleic acid fragments further comprises denaturing a plurality of nucleic acid fragments in a thermal cycler by applying heat to the plurality of nucleic fragments in solution.

13. A method as defined in claim 1, wherein measuring the size of particles in the solution further comprises:
    emitting light from a light source;
    dividing the emitted light from the light source into a first light path and a second light path;
    directing the first light path to a first container containing the plurality particles in the solution;
    directing the second light path to a second container containing a suspension material devoid of the plurality of particles in the solution;
    retrieving a first transmission value of the first light path through the first container;
    retrieving a second transmission value of the second light path through the second container;
    directing the first and second light paths to the second and first containers, respectively;
    retrieving a third transmission value of the first light path through the second container;
    retrieving a fourth transmission value of the second light path through the first container; and
    calculating a ratio of the first and second transmission values to the third and fourth transmission values to determine an indication of transmissivity for a given wavelength.

14. A computer-readable media having stored thereon computer executable instructions, wherein the instructions perform steps for providing a quantitative analysis of a target material via a computing device, comprising:
    measuring the size of a plurality particles in a solution, including, at least the size of a plurality of non-hybridized nucleic acid fragments, to predetermine a standard distribution of non-hybridized nucleic acid fragments;
    measuring the size of a plurality of particles in the solution, after introducing the target material;
    hybridizing at least one nucleic acid fragment with the target material if present in the solution; and
    at least one of detecting or quantifying the presence or non-presence of the target material by comparing the measured size of the particles after hybridizing to the standard distribution of non-hybridized nucleic acid fragments to determine whether at least a subset of the nucleic acid fragments have hybridized with the target material wherein no bead(s) is/are used in the quantification of said target material.

15. A computer-readable media as defined in claim 14, wherein measuring the size of the particles in solution further comprises causing a light measurement system to detect changes in the size of the particles.

16. A computer-readable media as defined in claim 15, wherein measuring the size of particles in solution further comprises causing the light measurement system to:
    emit light from a light source;
    divide the light from the light source into a first path and a second path;
    direct the first path to a first container containing the plurality of particles in the solution;
    direct the second path to a second container containing a suspension material devoid of the plurality of particles in the solution;
    retrieve a first transmission value of the first path through the first container;
    retrieve a second transmission value of the second path through the second container;
    direct the first and second paths to the second and first containers, respectively;
    retrieve a third transmission value of the first path through the second container;
    retrieve a fourth transmission value of the second path through the first container; and
    calculate a ratio of the first and second transmission values to the third and fourth transmission values to determine an indication of transmissivity for a given wavelength.

* * * * *